United States Patent [19]

Lamparter et al.

[11] Patent Number: 4,542,239
[45] Date of Patent: Sep. 17, 1985

[54] PROCESS FOR RECOVERING TEREPHTHALIC ACID FROM WASTE POLYETHYLENE TEREPHTHALATE

[75] Inventors: Richard A. Lamparter, Houghton, Mich.; Bruce A. Barna, Las Cruces, N. Mex.; David R. Johnsrud, North Brunswick, N.J.

[73] Assignee: Board of Control of Michigan Technological University, Houghton, Mich.

[21] Appl. No.: 501,805

[22] Filed: Jun. 7, 1983

Related U.S. Application Data

[63] Continuation of Ser. No. 322,474, Nov. 18, 1981, abandoned.

[51] Int. Cl.[4] .................... C07C 51/487; C07C 29/88
[52] U.S. Cl. .................................. 562/487; 562/485; 568/868; 568/871
[58] Field of Search ............... 562/483, 485, 487; 568/868, 871

[56] References Cited

U.S. PATENT DOCUMENTS 3,544,622 12/1970 England ........................ 562/483
3,849,489 11/1974 Rudzki .......................... 562/487 X
4,355,175 10/1982 Pusztaszeri ..................... 562/483

FOREIGN PATENT DOCUMENTS 822834 11/1959 United Kingdom .
1471093 4/1977 United Kingdom .

Primary Examiner—Natalie Trousof
Assistant Examiner—Vera C. Clarke

[57] ABSTRACT

Terephthalic acid (TPA) is recovered from used polyethylene terephthalate beverage containers by reacting comminuted containers in a reaction zone with an aqueous medium containing ammonium hydroxide at elevated temperatures and pressures to form a water soluble diammonium salt of TPA, separating any undissolved solids from the reaction product, acidifying the remaining reaction product to liberate TPA, and separating the precipitated TPA. A portion of the liquid remaining after separation of TPA can be mixed with lime or slaked lime, the resulting mixture treated in an ammonia stripper to remove ammonia therefrom and the ammonia overheads from the stripper blended with another portion of the liquid remaining after separation of TPA to form a stream containing ammonium hydroxide which is recycled to the reaction zone. Ethylene glycol can be recovered from the bottoms from the ammonia stripper by distillation.

17 Claims, 1 Drawing Figure

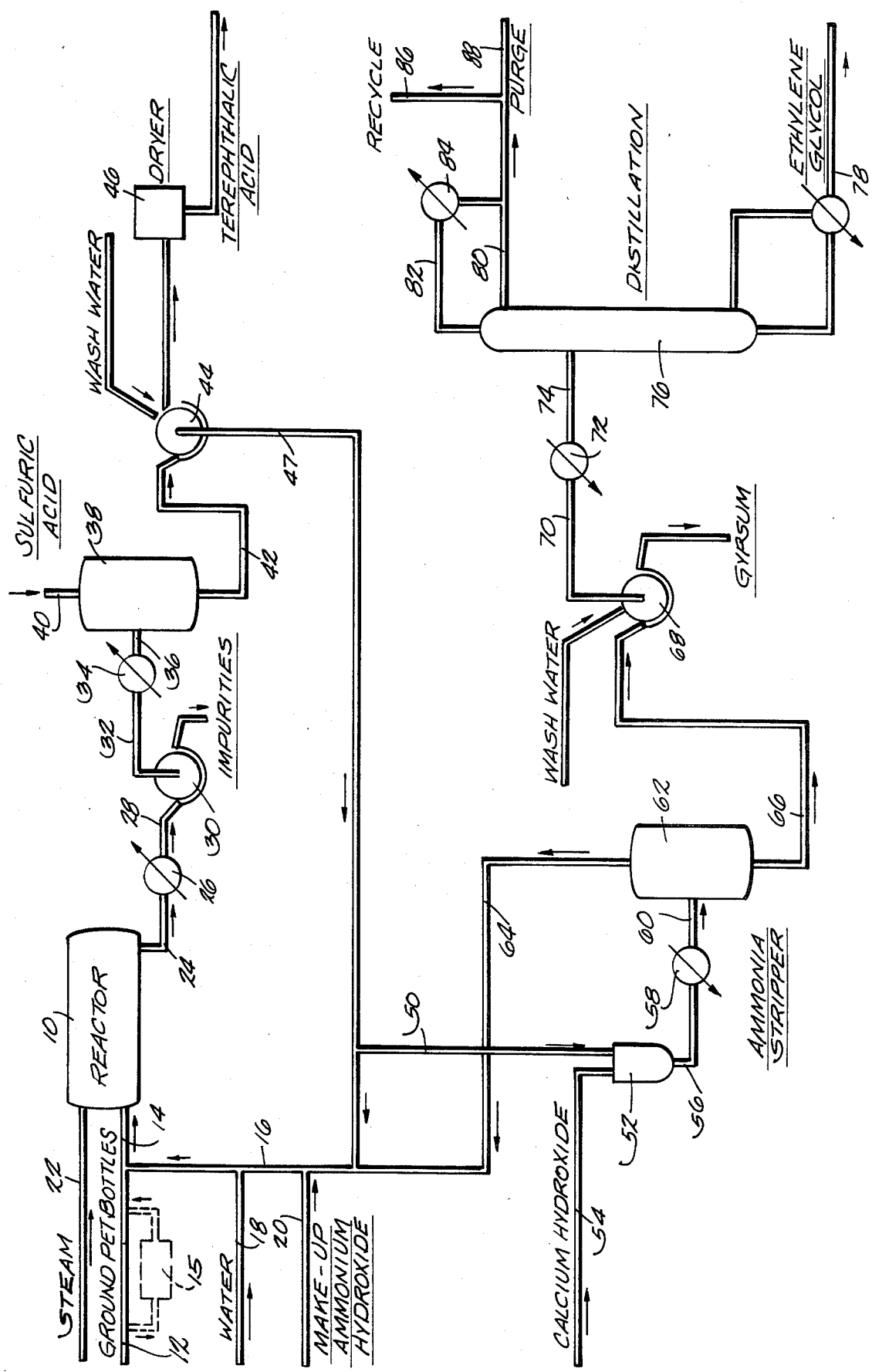

PROCESS FOR RECOVERING TEREPHTHALIC ACID FROM WASTE POLYETHYLENE TEREPHTHALATE

This is a continuation of application Ser. No. 322,474 filed Nov. 18, 1981, now abandoned.

BACKGROUND OF THE INVENTION

This invention relates to the recovery of a terephthalic acid from polyethylene terephthalate. In one aspect, this invention relates to recovery of terephthalic acid and ethylene glycol from waste products, such as beverage containers, made from polyethylene terephthalate.

Most polyester resins used in commercial applications are formed from raw materials which are rising in price and have relatively large markets. Accordingly, recovery of these raw materials from scrap, waste and used products is an important economical consideration as well as an ecological consideration. One widely used polyester is polyethylene terephthalate made from terephthalic acid and ethylene glycol.

Used bottles made from polyethylene terephthalate is a large potential source of recoverable terephthalic acid and ethylene glycol. It is estimated that from 375 to 500 million pounds of polyethylene terephthalate were used for beverage bottles in 1980. Recent legislation in several states requiring a deposit refundable upon return of all empty beverage containers has established an ongoing procedure for collecting and separating polyethylene terephthalate containers which must be disposed. Polyethylene terephthalate beverage containers cannot be reused because the elevated temperatures required for sterilization deforms the container.

Polyethylene terephthalate containers can be ground into small pieces for use as a filler material or remelted for formation of different articles. The polyethylene terephthalate recovered by such processes contains impurities, such as pigment, paper and metal from caps. Consequently, applications for the reclaimed polyethylene terephthalate are limited to non-food uses and low-purity molded products.

Several different techniques have been proposed for recovering terephthalic acid and ethylene glycol from polyethylene terephthalate. One technique involves depolymerization of polyethylene terephthalate by saponification.

In one approach for saponification, polyethylene terephthalate is reacted with an aliphatic alcohol and a dialkyl terephthalate is recovered. This approach is exemplified in U.S. Pat. Nos. 3,321,510, 3,403,115 and 3,501,420.

In a second approach, polyethylene terephthalate is reacted with an aqueous solution of an alkali metal hydroxide or carbonate (usually sodium hydroxide) at an elevated temperature to yield a water soluble salt of terephthalic acid and ethylene glycol. The reaction product is acidified to liberate terephthalic acid which is water insoluble and the terephthalic acid precipitate is separated by filtration or the like. This approach is exemplified by U.S. Pat. Nos. 3,377,519, 3,801,273 and 3,956,088. U.S. Pat. No. 3,544,622 discloses a variation to this approach wherein the reaction is carried out under conditions to produce a water insoluble salt of terephthalic acid which is separated, washed and then acidified to produce terephthalic acid.

Empty beverage containers recovered from the consumers commonly have aluminum caps lined with polyvinyl chloride or the like, wrap around polypropylene-coated paper labels bonded to the surface with a polyvinyl acetate adhesive, residual sugars and, in some cases, polyethylene base caps for strengthening purposes. Without costly controls, reaction conditions in the saponification processes disclosed in the above-noted patents tend to cause some dissolution of these extraneous materials which would become impurities in the recovered terephthalic acid and require costly purification. Therefore, various approaches have been considered for removing these materials from the containers prior to grinding or separating them from the polyethelene terephthalate after grinding. Such separation procedures represent a significant increase in the overall cost of recovery.

SUMMARY OF THE INVENTION

A principal object of the invention is to provide a simple and efficient process for recovering the raw materials from polyester waste products in economical yields and high purity form.

Another principal object of the invention is to provide a saponification process for recovering high purity terephthalic acid in economical yields from used polyethylene terephthalate beverage containers.

A further principal object of the invention is to provide a process described in the immediately proceeding paragraph wherein metal caps, labels and the like need not be removed prior to processing.

Other objects, aspects and advantages of the invention will become apparent to those skilled in the art upon reviewing the following detailed description, the drawing and appended claims.

Broadly, the process of the invention includes the steps of reacting polyethylene terephthalate scrap and/or waste in a reaction zone with an aqueous medium containing ammonium hydroxide at elevated temperature and pressure for a sufficient time to cleave the ester linkage and form a water soluble diammonium salt of terephthalic acid, separating any undissolved solids from the reaction product, acidifying the reaction product to liberate terephthalic acid and separating the precipitated terephthalic acid from the remainder. By using ammonium hydroxide in place of the stronger alkali metal bases, such as sodium hydroxide, used in conventional alkaline saponification processes, used polyethylene terephthalate beverage bottles can be processed without first removing aluminum caps, cap liners or labels and without washing to remove residual beverage. These extraneous materials are not attacked by the reaction medium and can be conveniently removed from reaction product by filtering or the like prior to the acidification step.

In accordance with a preferred embodiment for processing used polyethylene terephthalate beverage containers, calcium oxide or calcium hydroxide is mixed with a portion of the reaction product remaining after removal of terephthalic acid and ammonia is stripped from the resulting mixture and blended with the other portion of the remaining reaction product to form a stream containing ammonium hydroxide which is recycled to reaction zone. With this recycle scheme, the base being consumed is relatively inexpensive calcium oxide (lime) or calcium hydroxide (slaked lime). Hydrated calcium sulfate (gypsum) and ethylene glycol can be recovered from the bottoms from the ammonia stripper.

BRIEF DESCRIPTION OF THE DRAWING

The drawing is a diagrammatic representation of a process embodying the invention for recovering terephthalic acid and ethylene glycol from used polyethylene terephthalate beverage containers.

DESCRIPTION OF THE PREFERRED EMBODIMENTS

While the process of the invention can be used to treat a wide variety of polyethylene terephthalate scrap, it is particularly adaptable for processing used polyethylene terephthalate beverage containers and will be described for that use. As used hereinafter, the term "scrap" means scrap, waste and/or used products of polyethylene terephthalate.

Referring to the drawing, used polyethylene terephthalate beverage bottles, including aluminum caps and polyvinyl chloride liners, polypropylene-coated paper labels and polyethylene base caps (if present) are first comminuted (by grinding or the like) into a particle size suitable for pumping as part of an aqueous slurry. An aqueous slurry of the comminuted beverage bottles is pumped into a high pressure reactor 10 through conducts 12 and 14. Some of the base cap material can end up as an impurity in the final product. When a high purity product is desired and base caps are present, the base cap material preferably is removed from the slurry prior to introduction into the reactor 10, such as by a conventional flotation means 15 illustrated by dashed lines.

A portion of the filtrate from a terephthalic acid filter 44, containing water, ethylene glycol and ammonium sulfate, is blended with the ammonia overheads from an ammonia stripper 62 and the resulting mixture containing ammonium hydroxide is introduced into the reactor 10 through a recycle conduit 16 and conduit 14. Additional water required for the recycle stream and make-up ammonium hydroxide are introduced into the recycle conduit 16 through conduits 18 and 20, respectively. The remaining water and heat required to keep the reactor 10 at an elevated temperature and pressure to effect the desired dissolution or depolymerization of polyethylene terephthalate is supplied by steam injected into the reactor 10 through conduit 22.

The particle size of the ground bottles is not critical and is governed primarily by the particular pump or other mechanical means used for introducing the slurry into the reactor. The ratio of polyethelene terephthalate to water is also governed by that equipment and usually is in the order of 0.1:1 or so.

The reactor 10 is operated at a temperature of about 325° F. (163° C.) to about 550° F. (288° C.), preferably about 375° F. (191° C.) to about 450° F. (232° C.), and most preferably about 400° F. (204° C.). The reactor 10 is operated at a pressure above the vapor pressure of the liquid at the reaction temperature. The vapor pressure is about 100 to 1,000 psia for the broad temperature range, about 200 to 450 for the preferred temperature range and about 300 psia for the most preferred temperature. Accordingly, the reactor 10 usually is operated at a pressure ranging from about 450 to about 550 psig.

The ammonium hydroxide present in the reaction medium should be at least the stoichiometric amount for reacting with terephthalic acid and neutralizing it to form the diamonium salt thereof. Amounts of ammonium hydroxide up to about 3 times this stoichiometric amount can be used. Amounts less than this stoichiometric amount do not produce acceptable depolymerization of the polyethylene terephthalate and/or neutralization of the acid. On the other hand, little or no added benefit is realized with amounts in excess of about 3 times this stoichiometric amount The preferred amount of ammonium hydroxide is about 1.5 to 2.5 times the stoichiometric amount.

Ammonia hydroxide is more expensive than alkali metal hydroxides or carbonates used in conventional polyethylene terephthalate saponification processes. However, the maximum obtainable pH of the reaction medium is below a level where the aluminum bottle caps and other extraneous materials are attacked, thereby eliminating the need for costly controls for maintaining the pH of the reaction medium below a predetermined level or the need to remove the caps, labels or base caps before processing. Also, in the preferred embodiment illustrated, ammoninium hydroxide is recycled and the base actually consumed is lime or slaked lime, making the use of ammonium hydroxide cost effective.

The retention time in the reactor 10 is sufficient to dissolve all or substantially all of the polyethelene terephthalate and form the diammonium salt of terephthalic acid. This time can be as short as 1 to 2 minutes for higher temperatures and up to a maximum of about 180 minutes for the lower temperature. The preferred retention time is within a range of about 5 to 45 minutes.

The reactor 10 preferably is provided with suitable mixing or stirring means (not shown) for continuously stirring the reaction medium to accelerate the breakdown of polyethelene terephthalate and formation of the diammonium salt of terephthalic acid. While not necessary for cleaving the ester linkage, oxygen or an oxygen-containing gas, such as air, can be introduced into the reaction medium to effect wet oxidation or partial wet oxidation of organic materials which tend to reduce the ultimate produce impurity, such as base caps made from a plastic material other than polyethylene terephthalate.

If oxidizing conditions are employed, a wet oxidation reactor of the type disclosed in U.S. Pat. No. 3,852,192 and 3,870,631 can be used. Conditions for wet oxidation or partial wet oxidation, if used, can be similar to those disclosed in U.S. Pat. No.3,953,502. The disclosures of these three patents are incorporated herein by reference. The amount of oxidation should be kept to that required to combust the extraneous organic material introduced into the reaction medium from dirty beverage containers. Excessive oxidation can cause some loss of the terephthalic acid component.

A reaction product containing a water soluble diammonium salt of terephthalic acid and ethylene glycol is withdrawn from the reactor 10 through conduit 24, passed through a heat exchanger 26 to extract heat for use in preheating the recycle stream or the like and then passed through conduit 28 to a rotary drum filter 30 wherein a undissolved solid impurities, such as pigments, pieces of metal caps, cap liners and labels, are removed. The reaction product is filtered while still hot, for example, about 280° F. (138° C.), because the solubility of the terephthalate salt is higher at higher temperature and entrainment of the salt on the filter is minimized.

The filtrate from the filter 30 is withdrawn through a conduit 32, passed through a heat exchanger 34 for recovering heat which can be used somewhere else in the system and then passed through conduit 36 to an acidification reactor 38. In the acidification reactor 38, the filtrate is acidified to liberate and precipitate terephthalic acid with a strong mineral acid introduced into the reactor through conduit 40. Suitable acids include sulfuric, nitric, phosphoric and hydrochloric, with sulfuric being preferred because of its cost and effectiveness.

The acidified product comprising an aqueous slurry of the precipitated terephthalic acid is withdrawn from the acidification reactor 38 through conduit 42 and passed to a rotary drum filter 44 wherein the terephthalic acid is removed. The terephthalic acid filter cake removed from the filter 44 is dried in a suitable dryer 46 after washing and packaged for reuse. The recovered terephthalic acid usually will have a purity of 99% or higher with the major impurity being ammonium sulfate.

A filtrate from the filter 44 containing water, ethylene glycol and ammonium sulfate is withdrawn through conduit 47. A portion of this filtrate (approximately 44%), after being blended with the overheads from the ammonia stripper 62 to form a stream containing ammonium hydroxide, is recycled to the reactor 10 through conduit 16.

The remaining portion of the filtrate (56%) is passed through conduit 50 to a mixing tank 52 wherein it is mixed with calcium oxide (lime) or calcium hydroxide (slaked lime) introduced into the mixing tank 52 through conduit 54. The resulting mixture is withdrawn from the mixing tank 52 through conduit 56, passed through a heat exchanger 58 for heating to a temperature of about 195° F. (91° C.) and passed through conduit 60 to the ammonia stripper 62.

In the ammonia stripper 52, the lime or slaked lime reacts with ammonium sulfate present in the mixture to form hydrated calcium sulfate (gypsum). As heat is added to the ammonia stripper 62, ammonia is separated and passes overhead through conduit 64 for recycle to the reactor 10 along with a portion of the filtrate from filter 44 as described above.

A liquid bottoms product containing gypsum, water and ethylene glycol is withdrawn from the ammonia stripper 62 through conduit 66 and passed to a rotary drum filter 68 for removal of the gypsum. The filter cake from the filter 68 can be dried to produce essentially pure gypsum.

A filtrate containing water, ethylene glycol and a small amount of ammonium sulfate is withdrawn from the filter 68 through conduit 70 and passed through a heat exchanger 72 for preheating to a temperature of about 213° F. (101° C.) and passed through conduit 74 into a distillation column 76 for recovery of ethylene glycol. Ethylene glycol is withdrawn as the bottoms product from distillation column 76 through conduit 78.

The overhead product from distillation column 76 is composed of water and a small amount of ethylene glycol. A portion of the overheads is withdrawn through conduit 80. Another portion is withdrawn from conduit 82 and passed through heat exchanger 84 to extract heat which can be used for the ammonia stripper 62. The majority of the overheads from the distillation column 76 is recycled to the reactor 10 through conduit 86 and a small portion is bled or purged from the system through conduit 88 to maintain the proper balance of ethylene glycol.

Only two major waste streams are generated by the process, the dilute ethylene glycol stream purged from the overheads of the distillation column 76 and the gypsum cake from the filter 68. The ethylene glycol/water stream has a low chemical oxygen demand, particularly when the reactor 10 is operated under wet oxidation conditions, and requires only normal activated-sludge digestion. The gypsum filter cake can be dried to produce essentially pure gypsum containing a very small amount of ethylene glycol. It can be used in cement, drywall fillers for plastics and similar applications.

Without further elaboration, it is believed that one skilled in the art, using the foregoing descrition, can utilize the present invention to its fullest extent. The following example is presented to exemplify a preferred embodiment of the invention and should not be construed as a limitation thereof.

EXAMPLE

A system illustrated in the drawing for recovering terephthalic acid and ethylene glycol from used polyethylene terephthalate beverage containers including aluminum caps, polyvinyl chloride cap liners, polypropylene-coated paper labels and polyethylene base caps (if used) in accordance with the invention is operated under the following conditions:

| | |
|---|---|
| Reactor (4) | |
| Pressure, psig | 450 |
| Temperature, °F. | 400 |
| Steam, BTU/hr | 915,400 |
| PET bottles (conduit 12), lbs/hr | 830 |
| Reactor Outlet (conduit 24) | |
| Composition, lbs/hr | |
| Diammonium terephthalate | 860 |
| Ammonium sulfate | 918 |
| Ammonium hydroxide | 300 |
| Ethylene glycol | 493 |
| Water | 7,857 |
| Pigment, labels, caps, etc. (maximum) | 250 |
| Acidification Reactor (38) | |
| Inlet (conduit 36) temperature, °F. | 80 |
| Sulfuric acid, lbs/hr | 841 |
| Outlet (conduit 42) temperature, °F. | 100 |
| Outlet composition, lbs/hr | |
| Terephthalic acid | 713 |
| Ethylene glycol | 495 |
| Ammonium sulfate | 2,012 |
| Water | 7,857 |
| Filter (30) | |
| Water wash, lbs/hr | 713 |
| Filtrate composition (conduit 47), lbs/hr | |
| Ethylene glycol | 491 |
| Ammonium sulfate | 2,051 |
| Water | 8,011 |
| Filter cake composition, lbs/hr | |
| Terephthalic acid | 713 |
| Ethylene glycol | 2 |
| Ammonium sulfate | 7 |
| Water | 713 |
| Dried Terephthalic Acid Product (from dryer 46) | |
| Composition, lbs/hr | |
| Terephthalic acid | 713 |
| Ammonium sulfate | 7 |
| Mixing Tank (52) | |
| Calcium hydroxide, lbs/hr | 635 |
| Filtrate (conduit 50), lbs/hr | |
| Ethylene glycol | 278 |
| Ammonium hydroxide | 1,133 |
| Water | 4,425 |
| Ammonia Stripper (62) | |
| Overheads (conduit 64) | |
| Temperature, °F. | 195 |
| Composition, lbs/hr | |

| | |
|---|---:|
| Ammonium hydroxide | 603 |
| Water | 602 |
| Bottoms (conduit 66) | |
| Temperature, °F. | 195 |
| Composition, lbs/hr | |
| Ethylene glycol | 278 |
| Hydrated calcium sulfate (gypsum) | 1,467 |
| Water | 3,514 |
| Filter (68) | |
| Water wash, lbs/hr | 1,467 |
| Filtrate composition (conduit 70), lbs/hr | |
| Ethylene glycol | 273 |
| Hydrated calcium sulfate | 9 |
| Water | 3,514 |
| Filter cake composition, lbs/hr | |
| Hydrated calcium sulfate (gypsum) | 1,467 |
| Ethylene glycol | 5 |
| Water | 1,467 |
| Distillation Column (76) | |
| Inlet (conduit 74) temperature, °F. | 213 |
| Bottoms (conduit 78) | |
| Temperature, °F. | 347 |
| Composition, lbs/hr | |
| Ethylene glycol | 256 |
| Water | 1 |
| Overheads | |
| Temperature (conduit 80), °F. | 210 |
| Recycle composition (conduit 86), lbs/hr | |
| Water | 2,536 |
| Ethylene glycol | 15 |
| Purge composition (conduit 88), lbs/hr | |
| Water | 979 |
| Ethylene glycol | 6 |

From the foregoing description and example, it can be seen that process provided by the invention is capable of recovering the raw materials of scrap polyester in high yields and purity. In the specific preferred embodiment described in detail, high purity terephthalic acid can be recovered from used polyethylene terephthalate beverage containing without first removing metal caps or labels or washing to remove residual beverage and without costly control of the depolymerization reaction or costly purification techniques for removing impurities.

One skilled in the art can easily ascertain the essential characteristics of the process and, without departing from the spirit and scope of the invention, make various changes and modifications to adapt it to various usages.

We claim:

1. A process for recovering terephthalic acid from scrap polyethylene terephthalate comprising the steps of
    (a) reacting said scrap polyethylene terephthalate with an aqueous medium containing ammonium hydroxide at a temperature of at least 325° F. and at an elevated pressure from a time period sufficient to cleave the polyester linkage and form a water soluble diammonium salt of terephthalic acid which is maintained in solution during this reaction;
    (b) physically separating any undissolved solids from the resulting reaction product;
    (c) acidfying the remaining liquid with an acid to precipitate terephthalic acid; and
    (d) separating the precipitated terephthalic acid from the remainder.

2. A process according to claim 1 including the further steps of:
    (e) mixing calcium oxide or calcium hydroxide with the liquid remaining from step (d);
    (f) passing the resulting mixture to a stripping zone to strip ammonia therefrom; and
    (g) recycling the ammonia to the reaction zone.

3. A process according to claim 2 including the further steps of:
    (h) withdrawing a bottoms product from the stripping zone containing ethylene glycol.
    (i) separating solids from the bottoms product from the stripping zone; and
    (j) recovering ethylene glycol from the remaining liquid.

4. A process according to claim 1 wherein step (a) is carried out at a temperature within a range of about 325° to about 550° F.

5. A process according to claim 4 wherein said temperature is within a range of about 375° to about 450° F.

6. A process according to claim 1 wherein the reaction of step (a) is carried out for a time of about 1 to about 180 minutes.

7. A process according to claim 6 wherein said reaction time is about 5 to about 45 minutes.

8. A process according to claim 1 wherein the amount of ammonium hydroxide in the reaction medium is at least the stoichiometric amount required for forming the diammonium salt of terephthalic acid.

9. A process according to claim 8 wherein the amount of ammonium hydroxide in the reaction medium is up to 3 times the stoichiometric amount.

10. A process according to claim 9 wherein the amount of ammonium hydroxide in the reaction medium is about 1.5 to about 2.5 times the stoichiometric amount.

11. A process according to claim 1 wherein the acid used in step (c) is sulfuric acid.

12. A process for recovering terephthalic acid from used polyethylene terephthalate beverage containers comprising the steps of:
    (a) introducing an aqueous slurry of the beverage containers in comminuted form into a reaction zone;
    (b) reacting the polyethylene terephthalate in the reaction zone with an aqueous medium containing ammonium hydroxide at a temperature of at least 325° F. and at an elevated pressure for a time period sufficient to cleave the polyester linkage and form a water soluble salt of terephthalic acid which is maintained in solution during this reaction;
    (c) physically separating any undissolved solids from the resulting reaction product;
    (d) acidifying the remaining liquid to precipitate terephthalic acid; and
    (e) separating the precipitated terephthalic acid from the remainder.

13. A process according to claim 12 wherein the beverage containers in the slurry introduced into the reaction are comminuted without removing caps or labels.

14. A process according to claim 12 including the further steps of recovering ethylene glycol from the liquid remaining from step (e).

15. A process according to claim 12 including the further steps of:
    (f) mixing calcium oxide or calcium hydroxide with a portion of the liquid remaining from step (e);
    (g) passing the resulting mixture to a stripping zone to strip ammonia therefrom as overheads;
    (h) blending ammonia from the stripping zone with another portion of the liquid remaining from step (e) to form a stream containing ammonium hydroxide; and (i) recycling the resulting stream to the reaction zone.

16. A process according to claim 15 including the further steps of:
   (j) withdrawing a bottoms product from the stripping zone containing gypsum and ethylene glycol;
   (k) separating the gypsum from the bottoms products; and
   (1) recovering ethylene glycol from the liquid remaining from step (k).

17. A process according to claim 16 wherein the ethylene glycol is recovered by:
   (m) passing the remaining liquid to a distillation zone; and
   (n) recovering ethylene glycol as the bottoms from the distillation zone.

* * * * *